(12) United States Patent
McDonnell et al.

(10) Patent No.: US 6,297,022 B1
(45) Date of Patent: Oct. 2, 2001

(54) METHOD OF IDENTIFYING AGONISTS AND ANTAGONISTS FOR TUMOR NECROSIS RELATED RECEPTOR TR1

(75) Inventors: Peter C. McDonnell, Elkins Park, PA (US); Peter R Young, Lawrenceville, NJ (US); Jun Zou, Maple Glen, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/153,927

(22) Filed: Sep. 16, 1998

Related U.S. Application Data

(60) Provisional application No. 60/061,334, filed on Oct. 8, 1997.

(51) Int. Cl.[7] .................. G01N 33/567; G01N 33/566
(52) U.S. Cl. ............ 435/7.21; 435/252.3; 435/361; 435/7.1; 436/501; 530/350; 530/351; 536/23.5
(58) Field of Search .................. 530/350, 351; 536/23.5; 435/252.3, 361, 7.1, 7.21; 436/501

(56) References Cited

FOREIGN PATENT DOCUMENTS

| 0 308 378 A | 3/1989 | (EP) . |
|---|---|---|
| 0 816 380 A1 | 1/1998 | (EP) . |
| 0 867 509 A | 9/1998 | (EP) . |
| WO97/33902 | 9/1987 | (WO) . |
| WO96/28546 | 9/1996 | (WO) . |
| WO97/33904 | 9/1997 | (WO) . |
| WO99/00518 | 7/1999 | (WO) . |

OTHER PUBLICATIONS

Hahne, M. et al., Apr., a New Ligand of the Tumor Necrosis Factor Family Stimulates Tumor Cell Growth., J. Exp. Med., vol. 188, pp. 1185–1190, Sep. 1998.*

Pan, G. et al., "An antagonist receptor and a death domain–containing receptor for TRAIL", *Science*, 277 (8), Aug. 1997, pp. 815–818.

Sheridon, J.P. et al., "Control of TRAIL–induced apoptosis by a family of degnalling and decoy receptors" *Science*, vol. 277 (8), Aug. 1997, pp. 818–821.

Gura, T., "How TRAIL kills cancer cells but not normal cells." *Science*, vol. 277 (8), Aug. 1997, pp. 768.

Marsters et al., "identification of a ligand for the death domain" *Current Biology*, vol. 8, (9) Apr. 13, 1998, pp. 525–528.

* cited by examiner

*Primary Examiner*—Lorraine Spector
*Assistant Examiner*—Eileen B. O'Hara
(74) *Attorney, Agent, or Firm*—William T. Han; William T. King; Charles M. Kinzig

(57) ABSTRACT

The present invention relates to tumor necrosis factor receptor (TNF-R) related polypeptide and its ligand, hereinafter referred to as TR1 and TL3. The invention relates to methods to identify agonists and antagonists of TR1 and TL3.

10 Claims, No Drawings

US 6,297,022 B1

METHOD OF IDENTIFYING AGONISTS AND ANTAGONISTS FOR TUMOR NECROSIS RELATED RECEPTOR TR1

CROSS REFERENCE TO RELATED APPLICATION

This application claims priority to United States provisional application 60/061,334 filed Oct. 8, 1997.

FIELD OF INVENTION

The present invention relates to tumor necrosis factor receptor (TNF-R) related polypeptides (proteins) and their ligands, hereinafter referred to as TR1, TR3, TR5, and TL3. The invention also relates to inhibiting or activating the action of such polypeptides using agonists or antagonists by the screening methods described herein.

BACKGROUND OF THE INVENTION

Many biological actions are a response to certain stimuli and natural biological processes, and are controlled by factors, such as cytokines. These cytokines act through target cell receptors by engaging the receptor and producing an intracellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, ten members of the TNF ligand superfamily have been identified and thirteen members of the TNF-receptor superfamily have been characterized.

Among the ligands there are included TNF-a, lymphotoxin-a (LT-a, also known as TNF-b), LT-b (found in complex heterotrimer LT-a2-b), FasL, CD40L, CD27L, CD30L, 4-1BBL, OX40L and TRAIL ((Wiley et al. Immunity 3: 673–682 (1995)) All but one of these (LTa) are expressed as type II membrane proteins. The superfamily of TNF receptors includes the p55TNF receptor, p75TNF receptor, TNF receptor-related protein, FAS antigen or APO-1, CD40, CD27, CD30, 4-1BB, OX40, low affinity p75, NGF-receptor(Meager, A., Biologicals, 22:291–295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-linked immunodeficiency state characterized by high levels of immunoglubulin M and low levels of immunoglobulin G in plasma, indicating faulty T-cell-dependent B-cell activation (Allen, R. C. et al., Science 259:990 (1993)). Targeted mutations of the low affinity nerve growth factor receptor cause a disorder characterized by faulty sensory innovation of peripheral structures (Lee, K. F. et al, Cell 69:737 (1992)).

TNF and LT-a are capable of binding to two TNF receptors (the 55- and 75-kd TNF receptors). A large number of biological effects elicited by TNF and LT-a, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-a are involved in the pathogenesis of a wide range of diseases, including endotoxic shock, cerebral malaria, tumors, autoimmuine disease, AIDS and graft-host rejection (Beutler, B. and Von Huffel, C., Science 264:667–668 (1994)). Mutations in the p55 Receptor cause increased susceptibility to microbial infection.

Moreover, an about 80 amino acid domain near the C-terminus of TNFR1 (P55) and Fas was reported as the "death domain," which is responsible for transducing signals for programmed cell death (Tartaglia et al., Cell 74:845 (1993)). Other regions of the TNF receptor intracellular domain are responsible for the activation of transcription through NF-kB (Cheng and Baltimore Genes and Development 10: 963–973 (1996)). More recent evidence has suggested that receptors may induce signals in cells expressing membrane bound TNF family ligand in a process known as "reverse signaling" (Wiley et al., J. Immunol. 157:3635–3639.

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normal and in disease states. In particular, there is a need to isolate and characterize novel members of the TNF receptor family and their ligands.

This indicates that these Tumor necrosis factor receptors (TNF-R) and their ligands have an established, proven history as therapeutic targets. Clearly there is a need for identification and characterization of further members of Tumor necrosis factor receptor (TNF-R) family and their ligands which can play a role in preventing, ameliorating or correcting dysfunctions or diseases, including, but not limited to, chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atherosclerosis, and Alzheimers disease.

SUMMARY OF THE INVENTION

The present invention relates to tumor necrosis factor receptor (TNF-R) related polypeptides and their ligarids, hereinafter referred to as TR1, TR3, TR5, and TL3. The invention also relates to methods to identify agonists and antagonists of TR1, TR3, TR5 and TL3. The agonists and antagonists thus identified can be used to treat chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, bone diseases, cancer (eg lymphoproliferative disorders), atherosclerosis, and Alzheimers disease, among others, caused by imbalance of TR1, TR3, TR5, or TL3.

DESCRIPTION OF THE INVENTION

"TR1, or TR1 polypeptide or TR1 protein" refers, among others, generally to a polypeptide having the amino acid sequence set forth in SEQ ID NO: 1 as well as polypeptides comprising the amino acid sequence of SEQ ID NO: 1; and polypeptides comprising the amino acid sequence which have at least 70% identity to that of SEQ ID NO: 1 over its entire length. Furthermore, TR1 also refers to a polypeptide which comprises a sequence which has 70% identity to a fragment of SEQ ID NO: 1. "TR1 or TR1 polypeptide or TR1 protein" also includes derivatives, such as fusion proteins, of the above polypeptides, and some of these derivatives are further illustrated below.

"TR3 or TR3 polypeptide or TR3 protein" refers, among others, generally to a polypeptide having the amino acid sequence set forth in SEQ ID NO:2 as well as polypeptides comprising the amino acid sequence of SEQ ID NO: 2; and polypeptides comprising the amino acid sequence which have at least 70% identity to that of SEQ ID NO:3 over its entire length. Furthermore, TR3 also refers to a polypeptide which comprises a sequence which has 70% identity to a fragment of SEQ ID NO: 2. "TR3 or TR3 polypeptide or TR3 protein" also includes derivatives, such as fusion proteins, of the above polypeptides, and some of these derivatives are further illustrated below.

"TR5 or TR5 polypeptide or TR5 protein" refers, among others, generally to a polypeptide having the amino acid sequence set forth in SEQ ID NO:3 as well as polypeptides comprising the amino acid sequence of SEQ ID NO: 3; and polypeptides comprising the amino acid sequence which have at least 70% identity to that of SEQ ID NO:3 over its entire length. Furthermore, TR5 also refers to a polypeptide which comprises a sequence which has 70% identity to a fragment of SEQ ID NO: 3. "TR5 or TR5 polypeptide or TR5 protein" also includes derivatives, such as fusion proteins, of the above polypeptides, and some of these derivatives are further illustrated below.

"TL3 or TL3 polypeptide or TL3 protein" refers, among others, generally to a polypeptide having the amino acid sequence set forth in SEQ ID NO:4 as well as polypeptides comprising the amino acid sequence of SEQ ID NO: 4; and polypeptides comprising the amino acid sequence which have at least 70% identity to that of SEQ ID NO:4 over its entire length. Furthermore, TL3 also refers to a polypeptide which comprises a sequence which has 70% identity to a fragment of SEQ ID NO: 4. "TL3 or TL3 polypeptide or TL3 protein" also includes derivatives, such as fusion proteins, of above polypeptides, and some of these derivatives are further illustrated below.

The cDNA sequence encoding amino acid sequence of SEQ ID NO:4 is contained in SEQ ID NO: 11.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A.M., ed., Oxford University Press, New York, 1988; BIO-COMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCG program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polypeptide having an amino acid sequence having at least, for example, 70% "identity" to a reference amino acid sequence of SEQ ID NO:2 is intended that the amino acid sequence of the polypeptide is identical to the reference sequence except that the polypeptide sequence may include up to thirty amino acid alterations per each 100 amino acids of the reference amino acid of SEQ ID NO: 2. In other words, to obtain a polypeptide having an amino acid sequence at least 70% identical to a reference amino acid sequence, up to 30% of the amino acid residues in the reference sequence may be deleted or substituted with another amino acid, or a number of amino acids up to 30% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

We have now discovered that TL3 of SEQ ID NO: 4 is a ligand of TR1 of SEQ ID NO:1 (otherwise known as osteoprotegerin (OPG), W. S. Simonet, et al., *Cell*, Vol 89, pp 309–319, 1997). Further, we also discovered that TL3 of SEQ ID NO: 4 is a ligand of TR3 of SEQ ID NO: 2 (otherwise known as DR3). Further, we also discovered that TL3 of SEQ ID NO: 4 is a ligand of TR5 of SEQ ID NO: 3. Thus, the TR1, TR3 and TR5 polypeptides of the present invention, and their ligand, TL3, can be employed in a screening process for compounds which bind to the receptors, or to their ligands, and which activate (agonists) or inhibit activation of (antagonists) TR1, TR3 and TR5 receptor polypeptides of the present invention, or their ligand TL3. Thus, polypeptides of the invention may be used to assess the binding of small molecule substrates, receptors and ligands in, for example, cells, cell-free preparations, chemical libraries, and natural product mixtures. These substrates, receptors and ligands may be natural substrates and ligands, or may be structural or functional mimetics. See Coligan et al., *Current Protocols in Immunology* 1(2) :Chapter 5 (1991).

TR1, TR3, TR5, and TL3 polypeptides are responsible for many biological functions, including many pathologies. Accordingly, it is desirous to find compounds and drugs which stimulate TR1, TR3, TR5, or TL3 on the one hand; and which can inhibit the function of TR1, TR3, TR5, or TL3; or remove TR1, TR3, TR5, or TL3 expressing cells on the other (also defined as antagonists). Antagonists for TR1, TR3, TR5, and TL3 (including agents which remove TR1, TR3, TR5, or TL3 expressing cells) may be employed for a variety of therapeutic and prophylactic purposes for such conditions as chronic and acute inflammation, arthritis, septicemia, autoimmune diseases (e.g. inflammatory bowel disease, psoriasis), transplant rejection, graft vs. host disease, infection, stroke, ischemia, acute respiratory disease syndrome, restenosis, brain injury, AIDS, Bone diseases, cancer (e.g. lymphoproliferative disorders), atheroschlerosis, and Alzheimers disease. Agonists can be employed for therapeutic and prophylactic purposes for such conditions responsive to activation of T cells and other components of the immune system, such as for treatment of cancer and AIDS. However, agonists can also be employed for inappropriate stimulation of T cells and other components of the immune system which leads to down modulation of immune activity with therapeutic or prophylactic application for conditions such , as chronic and acute inflammation, arthritis, septicemia, autoimmune diseases (e.g. inflammatory bowel disease, psoriasis), transplant rejection, graft vs. host disease, infection, stroke, ischemia, acute respiratory disease syndrome, restenosis, brain injury, bone diseases, atheroschlerosis, and Alzheimers disease.

Antagonists may be identified using assays to detect compounds which inhibit binding of TL3 to TR1, TR3 or TR5 in either cell-free or cell based assays. Suitable cell-free assays may be readily determined by one of skill in the art. For example, an ELISA format may be used in which purified TR1, TR3 or TR5, or a purified derivative of TR1, TR3 or TR5, such as a fusion protein, containing the extracellular domain of TR1, TR3 or TR5, is immobilized on a suitable surface, either directly or indirectly (e.g., via an antibody to TR1, TR3 or TR5 or to the fused epitope or protein domain) and candidate compounds are identified by their ability to block binding of purified soluble, extracellular domain of TL3 to TR1, TR3 or TR5. The binding of TL3 to TR1, TR3, or TR5 could be detected by using a label directly or indirectly associated with TL3. Suitable detection systems include the streptavidin horseradish peroxidase conjugate, or direct conjugation by a tag, e.g., fluorescein. Conversely, purified, soluble TL3 may be immobilized on a suitable surface, and candidate compounds identified by their ability to block binding of purified TR1, TR3 or TR5 to TL3. The binding of TR1, TR3 or TR5 to TL3 could be detected by using a label directly or indirectly associated with TR1, TR3 or TR5. Many other assay formats are possible that use the TR1, TR3 or TR5 protein and its ligand.

Suitable cell based assays may be readily determined by one of skill in the art. In general, such screening procedures involve producing appropriate cells which express the receptor polypeptides (or ligands thereof) of the present invention on the surface thereof. Such cells include cells from mammals, yeast, Drosophila or *E. coli*. Cells expressing the receptor, such as TR1, TR3 or TR5, (or cell membrane containing the expressed receptor) are then contacted with a test compound to observe binding, or stimulation or inhibition of a functional response. The assays may simply test binding of a candidate compound wherein adherence to the cells bearing the receptor is detected by means of a label directly or indirectly associated with the candidate compound or in an assay involving competition with a labeled competitor, such as the ligand TL3. Alternatively, cells expressing the ligand, such as TL3, (or cell membrane containing the expressed ligand) are then contacted with a receptor, such as TR1, TR3 or TR5, or test compound to observe binding, or stimulation or inhibition of a functional response. Similarly, the assays may simply test binding of a candidate compound wherein adherence to the cells bearing the ligand is detected by means of a label directly or indirectly associated with the candidate compound or in an assay involving competition with a labeled competitor, such as the receptors TR1, TR3 and TR5. Further, these assays may test whether the candidate compound results in a signal generated by activation of the receptor (e.g TR1, TR3 or TR5) or its respective ligand (e.g. TL3) using detection systems appropriate to the cells bearing the receptor or its ligand and fusion proteins thereof at their surfaces. Typical fusion partners include fusing the extracellular domain of the receptor or ligand with the intracellular tyrosine kinase domain of a second receptor. Inhibitors of activation are generally assayed in the presence of an agonist, such as the ligand TL3 for cells expressing TR1, TR3 or TR5 receptors or receptor fusions respectively; or the receptor TR1, TR3 or TR5 with cells expressing TL3 ligands or ligand fusions, and the effect on activation by the agonist by the presence of the candidate compound is observed. Standard methods for conducting such screening assays are well understood in the art.

Examples of potential TR1, TR3 or TR5 antagonists include antibodies or, in some cases, proteins which are closely related to the ligand of the TR1, TR3 or TR5, e.g., a fragment of the respective ligand TL3, or small molecules which bind to the receptor, or its ligand, but do not elicit a response, so that the activity of the receptor is prevented. Examples of potential TR1, TR3 or TR5 agonists include antibodies that bind to TR1, TR3 or TR5, its respective ligand, such as TL3, or derivatives thereof, and small molecules that bind to TR1, TR3 or TR5. These agonists will elicit a response mimicking all or part of the response induced by contacting the native ligand.

Since receptors may also invoke signals in cells expressing the membrane TL3, these screens may also yield agonists which mimic the agonist activity of TR1, TR3 or TR5 with membrane TL3. Examples of potential TL3 agonists include antibodies that bind to TL3, its respective receptor, such as TR1, TR3 or TR5, or derivatives thereof, and small molecules that bind to TL3. These agonists will elicit a response mimicking all or part of the response induced by contacting the native ligand. Alternatively, TR1, TR3 or TR5 may be expressed as a soluble protein, including versions which fuse all or part of TR1, TR3 or TR5 with a convenient partner peptide for which detection reagents are available, eg TR1-IgG, TR3-IgG or TR5-IgG fusions, and used in a solid state or solution phase binding assay. For example, the soluble TR1, TR3 or TR5 can be used to detect agonist or antagonist binding directly through changes that can be detected experimentally, eg surface plasmon resonance, nuclear magnetic resonance spectrometry, sedimentation, calorimetry. The soluble TR1, TR3 or TR5 can be used to detect agonist or antagonist binding indirectly by looking for competition of the candidate agonist or antagonist with a ligand, such as TL3, whose binding can be detected. Ligand detection methods include antibody recognition, modification of the ligand via radioactive labeling, chemical modification (eg biotinylation), fusion to an epitope tag. Methods include ELISA based assays, immunoprecipitation and scintillation proximity. Assays similar to those described above using soluble or membrane bound TR1, TR3 or TR5 may also be used to identify and purify additional natural ligand (s) of TR1, TR3 or TR5. These ligands may be agonists or antagonists of the receptor Thus the invention relates to:

I. A method for identifying agonists or antagonists to TR1, TR3 or TR5 comprising:
(a) contacting a candidate compound with TR1, TR3 or TR5 in the presence of labeled or unlabeled ligand TL3 respectively; and
(b) assessing the ability of said candidate compound to compete with TL3 binding to TR1, TR3 or TR5 respectively;

II. The method of I in which TR1, TR3 or TR5 is on the surface of a host cell, on a cell membrane or on a solid support;

III. The method of II for identifying agonists which further includes determining whether the candidate compound affects a signal generated by TR1, TR3 or TR5 polypeptide at the surface of the cell, wherein a candidate compound which increases production of said signal is identified as an agonist;

IV. An agonist identified by the method of I, II or III;

V. The method of II for identifying antagonists which further includes determining whether the candidate compound affects a signal generated by TR1, TR3 or TR5 polypeptide at the surface of the cell, wherein a candidate compound which diminishes production of said signal is identified as an antagonist;

VI. An antagonist identified by the method of I, II or V;

VII. A method for identifying agonists or antagonists to TL3 comprising:
(a) contacting a candidate compound with TL3 in the presence of labeled or unlabeled TR1, TR3 or TR5 respectively; and
(b) assessing the ability of said candidate compound to compete with TR1, TR3 or TR5 binding to TL3;

VIII. The method of VII in which TL3 is on the surface of a host cell, on a cell membrane or on a solid support;

IX. The method of VIII for identifying agonists to TL3 which includes determining whether the candidate compound affects a signal generated by TL3 polypeptide at the surface of the cell, wherein a candidate compound which increases production of said signal is identified as an agonist;

X. An agonist identified by the method of IX;

XI. The method of VIII for identifying antagonists which further includes determining whether the candidate compound affects a signal generated by TL3 polypeptide at the surface of the cell, wherein a candidate compound which diminishes production of said signal is identified as an antagonist; and XII. An antagonist identified by the method XI Thus in another aspect, the present invention relates to a screening kit for identifying agonists, antagonists, ligands, receptors, substrates, enzymes, etc. for TR1, TR3, TR5, or TL3 polypeptides; which comprises:
(a) a TR1, TR3, TR5, or TL3 polypeptide, preferably that of SEQ ID NO:1, 2, 3 or 4;
(b) a recombinant cell expressing a TR1, TR3, TR5, or TL3 polypeptide, preferably that of SEQ ID NO: 1, 2,3 or 4;
(c) a cell membrane expressing a TR1, TR3, TR5, or TL3 polypeptide; preferably that of SEQ ID NO: 1, 2,3or4; or
(d) antibody to a TR1, TR3, TR5, or TL3 polypeptide, preferably that of SEQ ID NO: 1, 2, 3 or 4.

It will be appreciated that in any such kit, (a), (b), (c) or (d) may comprise a substantial component.

Prophylactic and Therapeutic Methods

This invention provides methods of treating an abnormal conditions related to both an excess of and insufficient amounts of TR1, TR3, TR5, or TL3 polypeptide activity.

If the activity of TR1, TR3, TR5, or TL3 polypeptide is in excess, several approaches are available. One approach comprises administering to a subject an inhibitor compound (antagonist) as hereinabove described along with a pharmaceutically acceptable carrier in an amount effective to inhibit activation by blocking binding of ligands to the TR1, TR3 or TR5 polypeptide, or by inhibiting a second signal, and thereby alleviating the abnormal condition.

In another approach, soluble forms of TR1, TR3 or TR5 polypeptides still capable of binding the ligand in competition with endogenous TR1, TR3 or TR5 polypeptide may be administered. Typical embodiments of such competitors comprise fragments of the TR1, TR3 or TR5 polypeptide.

For treating abnormal conditions related to an under-expression of TR1, TR3, TR5, or TL3 and its activity, several approaches are also available. One approach comprises administering to a subject a therapeutically effective amount of a compound which activates TR1, TR3, TR5, or TL3 polypeptide, i.e., an agonist as described above, in combination with a pharmaceutically acceptable carrier, to thereby alleviate the abnormal condition.

Formulation and Administration

Agonists and antagonists of TR1, TR3, TR5, or TL3 may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide or compound, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

The examples below are carried out using standard techniques, which are well known and routine to those of skill in the art, except where otherwise described in detail. The examples illustrate, but do not limit the invention.

EXAMPLES

The expression and determination of receptor ligand pairings for TL3, TR1, TR3 and TR5 are described below. TR1 is also known as osteoprotegerin (Simonet et al., Cell 89:309–319 (1997)). TR3 is also known as DR3, Apo3 or WSL-1 or LARD (Chinnaiyan, A. M. et al., Science 274:990–992 (1996); Marsters, S. A. et al., Curr. Biol. 6:1669–1676 (1996); Kitson, J. et al. Nature 384:372–375 (1996); Screaton, G. R. Proc. Natl. Acad. Sci. USA 94:4615–4619 (1997)). TR5 is also known as TRID or DcR1 (Pan, G. et al., Science 277:815–818 (1997); Sheridan et al., Science 277:818–820 (1997)).

Expression

TR1, TR3 and TR5 were expressed as fusion proteins in which the extracellular domain of either receptor was fused at its amino terminus with the hinge-CH2-CH3 region of human IgG1. The junction between the two protein domains was engineered to include the amino acid sequence for proteolytic cleavage by Factor Xa. When expressed in this form in mammalian cells, the TR fusion proteins (TR1Fc, TR3Fc and TR5 Fc respectively) were secreted as dimeric proteins, and were purified by protein A or protein G sepharose. The non-fused soluble receptor was generated from the TR1Fc, TR3Fc or TR5Fc fusion by incubation with bovine Factor Xa and was purified away from the Fc portin by repassage over protein A sepharose and pooling of the flow through.

TL3 is a type II membrane proteins in which it is the C-terminus which is extracellular. It was expressed as a secreted fusion protein by engineering an expression DNA construct in which the DNA encoding a substantial part of the carboxyterminal region, which includes all of the residues homologous to mature TNF, was fused to an amino terminal epitope tag sequence, and an amino terminal hydrophobic signal sequence for secretion, detection and purification. When transfected into mammalian cells, these DNA constructs resulted in the secretion of soluble, epitope tagged fusion proteins (sTL3 ). Specific details of the construction of each expression vector are given below.

TR1

The sequence of TR1 did not show any transmembrane region by hydrophobicity plot (Goldman et al., (1) ). The entire coding region of TR1 minus the terminator codon was therefore used to produce an Fc fusion construct. The TR2 insert in the vector TR2Fclink was replaced with TR1. TR2FcLink encodes amino acids 1–192 of TR2, followed by the amino acids RSIEGRGT for Factor Xa cleavage, followed by residues 226–458 (end) of human IgG1. The IgG1 region also has a mutation of Cys230 to Ala (2). The 3' end of TR1 was amplified from a TR1 cDNA using the following primers: 5' cgc ccc ttg ccc tga cca cta 3' (SEQ ID NO: 5) (upstream of HindIII site) and 5' gcc att tca gat ctt aag cag ctt att ttt act ga 3' (SEQ ID NO: 6) (replaces stop codon with BglII site). The PCR products were cloned into pCR2 (Invitrogen; pCR2TR1) and sequenced. The vector TR2Fclink was digested with EcoRI BglII and calf intestinal phosphatase, then ligated with the EcoRI/HindIII fragment of TR1 cDNA and HindIII/BglII fragment of pCR2TRI to form TR1Fclink.

COS cells were transiently transfected with TR1Fclink and the resulting supernatant was immunoprecipitated with protein A agarose. Western blot analysis of the immunoprecipitate using goat anti-human Fc antibodies revealed a strong band consistent with the expected size for glycosylated TR1Fc.

CHO cells were transfected with TR2Fclink to produce stable cell lines. Five lines were chosen by dot blot analysis for expansion and were adapted to shake flasks. The line with the highest level of TR2Fc protein expression was chosen by Western blot analysis.

TR3

The extracellular domain of TR3 was PCRed from a full length TR3 cDNA using the following two synthetic oligonucleotide primers: 5' gcc acc atg gaa caa cgc cct aga gga tgt gct gcc gtg gcc gcc gcg ctc ctc ctg gtg ctg ct 3' (SEQ ID NO: 7); 5' tgg acc caa gat ctc tgc ctc cat cca cag aca gc 3' (SEQ ID NO: 8). The PCR product was cloned into pCR2.1 (Invitrogen) and confirmed by sequencing. The EcoRI-BglII fragment of this plasmid was subcloned into the EcoRI-BglII vector fragment of TR2Fclink, replacing the TR2 fragment (see above under TR1 for description of this plasmid) to generate TR3Fclink. TR3Fclink clones were confirmed by restriction enzyme digestion. Transient transfection of clone TR3Fclink into COS cells, followed by immunoprecipitation and Western analysis of the resulting supernatant showed a single band of approximately 55 kD.

A similar protein was expressed upon transfection of CHO cells, and was purified by protein G sepharose chromatography.

TR5

Two synthetic oligonucleotide primers were used to PCR the extracellular domain of TR5: 5' gcc gcc gag atg caa ggg gtg aag gag 3' (SEQ ID NO: 9) and 5' atg gtg caa gat ctg taa tga gaa gag g 3' (SEQ ID NO: 10). The PCR products were cloned into pCR2.1 (Invitrogen) and sequenced. The EcoRI-BglII fragment of a clone with the expected sequence was subcloned into the EcoRI-BglII vector fragment of TR2Fclink, replacing the TR2 insert, and the product called TR5Fclink. TR5Fclink clones were confirmed by restriction enzyme digestion. Transient transfection of clone TR5Fclink into COS cells, followed by immunoprecipitation and Western analysis of the resulting supernatant showed a band larger than the expected size of 56.6 kD, indicating that the protein is probably glycosylated. Transfection of the same plasmid into CHO cells gave a similar product.

TL3

In order to express a soluble form of TL3 protein from CHO cells, a mammalian expression vector was constructed. A cDNA fragment of TL3 protein was created by PCR which started immediately after the putative transmembrane region and ended at the C-terminus. This corresponds to amino acid residues 51 (QQTELQ) to 250 (GFVKL). The gene was tagged at its amino-terminus by an anti-gp 120 mAb epitope, followed by 6 His residues and a factor Xa cleavage site (IEGR) for easy detection and purification and generation of the mature untagged protein. BamHI and EcoRV sites were created at ends of the PCR fragment encoding this TL3 fusion protein gene to facilitate its subcloning into the mammalian expression vector pCDTN which contains a tPA leader peptide and CMV promoter. The vector was transfected into both COS cells and CHO cells and the expression of secreted TL3 protein was confirmed by precipitation from cell medium by Ni-NTA and then immunoblotting with a monoclonal antibody to the gp120 epitope peptide attached to the TL3 protein. The protein band of TL3 was seen as ~32 kDa and the calculated molecular weights for TL3 protein is 25 kDa. The difference between the observed and the calculated molecular weight of TL3 protein is likely due to protein glycosylation.

During large scale expression of TL3 in CHO cells, TL3 was found to be cleaved to a 18 kDa protein. Amino terminal sequencing showed that this protein had lost both epitope tags and 79 N-terminal amino acids resulting in a protein which started at residue (starting amino acids: AVLTQK). This 18 kDa protein was used for TL3 functional characterization.

Binding studies

Receptor precipitation

We examined the ability of TR1Fc and TR2Fc to precipitate TL3 in solution followed by detection of the ligand in a western blot using antibodies against the fused epitope tag the ligands or the ligand itself. In a typical experiment, 2ug of TR1Fc or TR2Fc receptor was incubated with 250ng of purified TL3 in binding buffer (25 mM HEPES pH 7.2, 0.1% BSA, 0.01% TWEEN in RPMI 1640). After binding for four hours, receptor complexes were captured on protein A sepharose, centrifuged, washed with binding buffer, electrophoresed on 15% SDS PAGE and transferred for western blotting. TL3 was detected by a 1:5000 dilution of a mouse polyclonal antiserum raised to TL3 expressed and purified from superntants of CHO cells as described above, and was found to bind to TR1Fc, TR3Fc and TR5Fc but not to other TNFR related Fc fusion proteins.

Alternatively, the purified TL3 protein was labeled by I-125 and $1.5 \times 10^5$ cpm of the labeled TL3 (Final concentration=~1 nM) was incubated with 2 ug of each purified protein: TR1-Fc, TR1-Fc (with 10 ug of TR1), TR2-Fc, TR3-Fc and TR6-Fc or COS media containing TR5-Fc at 4 C. for overnight, followed by protein A-Sepharose precipitation. The pellets was washed and run on 14% SDS-PAGE. The dried gel was exposed to a x-ray film. I-125 labeled TL3 protein was found to be precipitated by TR1-Fc and competed off by excess of TR1 without Fc.

The references cited in this EXAMPLES section are as follows:

1. Engelman-DM; Steitz-TA; Goldman-A. Identifying nonpolar transbilayer helices in amino acid sequences of membrane proteins. Annu-Rev-Biophys-Biophys-Chem. 1986; 15: 321–53.
2. Johanson-K; Appelbaum-E; Doyle-M; Hensley-P; Zhao-B; Abdel-Meguid-SS; Young-P; Cook-R; Carr-S; Matico-R; et-al. Binding interactions of human interleukin 5 with its receptor alpha subunit. Large scale production, structural, and functional studies of Drosophila-expressed recombinant proteins. J-Biol-Chem. Apr. 21, 1995; 270(16): 9459–71.
3. Kumar-S; Minnich-MD; Young-PR. ST2/T1 protein functionally binds to two secreted proteins from Balb/c 3T3 and human umbilical vein endothelial cells but does not bind interleukin 1. J-Biol-Chem. Nov. 17, 1995; 270(46): 27905–13.
4. Johnsson, B., Lofas, S. And Lindquist, G. (1991). Immobilization of proteins to a carboxymethyldextran-modified gold surface for biospecific interaction analysis in surface plasmon resonance sensors. Anal. Biochem. 198:268–277.

What is claimed is:

1. A method of identifying compounds which inhibit the binding of the polypeptide of SEQ ID NO: 4 to the polypeptide of SEQ ID NO: 1 comprising:
    (a) contacting a candidate compound with the polypeptide of SEQ ID NO: 1 in the presence of a labeled or unlabeled polypeptide of SEQ ID NO: 4; and
    (b) assessing the ability of said candidate compound to compete with the binding of a labeled or unlabeled polypeptide of SEQ ID NO: 4 to the polypeptide of SEQ ID NO: 1.

2. A method of identifying compounds which inhibit the binding of the polypeptide of SEQ ID NO: 1 to the polypeptide of SEQ ID NO: 4, comprising:
    (a) contacting a candidate compound with the polypeptide of SEQ ID NO: 4 in the presence of a labeled or unlabeled polypeptide of SEQ ID NO: 1; and
    (b) assessing the ability of said candidate compound to compete with the binding of a labeled or unlabeled polypeptide of SEQ ID NO: 1 to the polypeptide of SEQ ID NO: 4.

3. A method of identifying candidate agonists or antagonists to the polypeptide of SEQ ID NO: 1, comprising:
    (a) contacting a candidate compound with the polypeptide of SEQ ID NO: 1 in the presence of a labeled or unlabeled polypeptide of SEQ ID NO:4; and
    (b) assessing the ability of said candidate compound to compete with the binding of a labeled or unlabeled polypeptide of SEQ ID NO: 4 to the polypeptide of SEQ ID NO: 1,
    (c) wherein if said candidate competes with the binding of said labeled or unlabeled polypeptide, it is a candidate agonist or antagonist.

4. The method of claim 3 in which the polypeptide of SEQ ID NO: 1 is on the surface of a host cell, on a cell membrane, or on a solid support.

5. The method of claim 4 for identifying agonists which further includes determining whether the candidate compound identified in step b affects a signal generated by the polypeptide of SEQ ID NO: 1 at the surface of said host cell, wherein a candidate compound which increases the production of said signal compared to the presence of the polypeptide of SEQ ID NO: 4 alone is identified as an agonist.

6. The method of claim 4 for identifying antagonists which further includes determining whether the candidate compound of step b affects a signal generated by the polypeptide of SEQ ID NO: 1 at the surface of the cell, wherein a candidate compound which diminishes the production of said signal compared to the presence of the polypeptide of SEQ ID NO: 4 alone is identified as an antagonist.

7. A method of identifying candidate agonists or antagonists to the polypeptide of SEQ ID NO: 4, comprising:
    (a) contacting a candidate compound with the polypeptide of SEQ ID NO: 4 in the presence of a labeled or unlabeled polypeptide of SEQ ID NO: 1; and
    (b) assessing the ability of said candidate compound to compete with the binding of a labeled or unlabeled polypeptide of SEQ ID NO: 1 to the polypeptide of SEQ ID NO: 4,
    (c) wherein if said candidate competes with the binding of said labeled or unlabeled polypeptide, it is a candidate agonist or antagonist.

8. The method of claim 7 in which the polypeptide of SEQ ID NO: 4 is on the surface of a host cell, on a cell membrane or on a solid support.

9. The method of claim 8 for identifying agonists which further includes determining whether the candidate compound identified in step b affects a signal generated by the polypeptide of SEQ ID NO: 4 at the surface of said host cell, wherein a candidate compound which increases the production of said signal compared to the presence of the polypeptide of SEQ ID NO: 1 alone is identified as an agonist.

10. The method of claim 8 for identifying antagonists which further includes determining whether the candidate compound of step b affects a signal generated by the polypeptide of SEQ ID NO: 4 at the surface of the cell, wherein a candidate compound which diminishes the production of said signal compared to the presence of the polypeptide of SEQ ID NO: 1 alone is identified as an antagonist.

* * * * *

SEQUENCE LISTING

<160> NUMBER OF SEQ ID NOS: 11

<210> SEQ ID NO 1
<211> LENGTH: 401
<212> TYPE: PRT
<213> ORGANISM: Human

<400> SEQUENCE: 1

-continued

```
Met Asn Lys Leu Leu Cys Cys Ala Leu Val Phe Leu Asp Ile Ser Ile
 1               5                  10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
                35                  40                  45

Tyr Leu Lys Gln His Cys Thr Ala Lys Trp Lys Thr Val Cys Ala Pro
        50                  55                  60

Cys Pro Asp His Tyr Tyr Thr Asp Ser Trp His Thr Ser Asp Glu Cys
 65              70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
                115                 120                 125

Gly Val Val Gln Ala Gly Thr Pro Glu Arg Asn Thr Val Cys Lys Arg
        130                 135                 140

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Thr Gln Lys
            165                 170                 175

Gly Asn Ala Thr His Asp Asn Ile Cys Ser Gly Asn Ser Glu Ser Thr
                180                 185                 190

Gln Lys Cys Gly Ile Asp Val Thr Leu Cys Glu Glu Ala Phe Phe Arg
            195                 200                 205

Phe Ala Val Pro Thr Lys Phe Thr Pro Asn Trp Leu Ser Val Leu Val
        210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
            245                 250                 255

Trp Lys His Gln Asn Lys Asp Gln Asp Ile Val Lys Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
        290                 295                 300

Lys Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
                355                 360                 365

Ile Arg Phe Leu His Ser Phe Thr Met Tyr Lys Leu Tyr Gln Lys Leu
        370                 375                 380

Phe Leu Glu Met Ile Gly Asn Gln Val Gln Ser Val Lys Ile Ser Cys
385                 390                 395                 400

Leu
```

```
<210> SEQ ID NO 2
<211> LENGTH: 417
<212> TYPE: PRT
<213> ORGANISM: Human

<400> SEQUENCE: 2

Met Glu Gln Arg Pro Arg Gly Cys Ala Ala Val Ala Ala Leu Leu
 1               5                  10                  15

Leu Val Leu Leu Gly Ala Arg Ala Gln Gly Gly Thr Arg Ser Pro Arg
                20                  25                  30

Cys Asp Cys Ala Gly Asp Phe His Lys Lys Ile Gly Leu Phe Cys Cys
            35                  40                  45

Arg Gly Cys Pro Ala Gly His Tyr Leu Lys Ala Pro Cys Thr Glu Pro
50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
                100                 105                 110

Thr Arg Cys Gly Cys Lys Pro Gly Trp Phe Val Glu Cys Gln Val Ser
            115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
                165                 170                 175

Val Ser Cys Pro Thr Ser Thr Leu Gly Ser Cys Pro Glu Arg Cys Ala
            180                 185                 190

Ala Val Cys Gly Trp Arg Gln Met Phe Trp Val Gln Val Leu Leu Ala
        195                 200                 205

Gly Leu Val Val Pro Leu Leu Leu Gly Ala Thr Leu Thr Tyr Thr Tyr
    210                 215                 220

Arg His Cys Trp Pro His Lys Pro Leu Val Thr Ala Asp Glu Ala Gly
225                 230                 235                 240

Met Glu Ala Leu Thr Pro Pro Ala Thr His Leu Ser Pro Leu Asp
                245                 250                 255

Ser Ala His Thr Leu Leu Ala Pro Pro Asp Ser Ser Glu Lys Ile Cys
                260                 265                 270

Thr Val Gln Leu Val Gly Asn Ser Trp Thr Pro Gly Tyr Pro Glu Thr
            275                 280                 285

Gln Glu Ala Leu Cys Pro Gln Val Thr Trp Ser Trp Asp Gln Leu Pro
    290                 295                 300

Ser Arg Ala Leu Gly Pro Ala Ala Ala Pro Thr Leu Ser Pro Glu Ser
305                 310                 315                 320

Pro Ala Gly Ser Pro Ala Met Met Leu Gln Pro Gly Pro Gln Leu Tyr
                325                 330                 335

Asp Val Met Asp Ala Val Pro Ala Arg Arg Trp Lys Glu Phe Val Arg
            340                 345                 350

Thr Leu Gly Leu Arg Glu Ala Glu Ile Glu Ala Val Glu Val Glu Ile
        355                 360                 365

Gly Arg Phe Arg Asp Gln Gln Tyr Glu Met Leu Lys Arg Trp Arg Gln
    370                 375                 380
```

```
Gln Gln Pro Ala Gly Leu Gly Ala Val Tyr Ala Ala Leu Glu Arg Met
385                 390                 395                 400

Gly Leu Asp Gly Cys Val Glu Asp Leu Arg Ser Arg Leu Gln Arg Gly
                405                 410                 415

Pro

<210> SEQ ID NO 3
<211> LENGTH: 299
<212> TYPE: PRT
<213> ORGANISM: Human

<400> SEQUENCE: 3

Met Gln Gly Val Lys Glu Arg Phe Leu Pro Leu Gly Asn Ser Gly Asp
1               5                   10                  15

Arg Ala Pro Arg Pro Asp Gly Arg Gly Val Arg Pro Arg Thr
            20                  25                  30

Gln Asp Gly Val Gly Asn His Thr Met Ala Arg Ile Pro Lys Thr Leu
            35                  40                  45

Lys Phe Val Val Ile Val Ala Val Leu Leu Pro Val Leu Ala Tyr
    50                  55                  60

Ser Ala Thr Thr Ala Arg Gln Glu Glu Val Pro Gln Gln Thr Val Ala
65                  70                  75                  80

Pro Gln Gln Gln Arg His Ser Phe Lys Gly Glu Cys Pro Ala Gly
                85                  90                  95

Ser His Arg Ser Glu His Thr Gly Ala Cys Asn Pro Cys Thr Glu Gly
                100                 105                 110

Val Asp Tyr Thr Asn Ala Ser Asn Asn Glu Pro Ser Cys Phe Pro Cys
            115                 120                 125

Thr Val Cys Lys Ser Asp Gln Lys His Lys Ser Ser Cys Thr Met Thr
130                 135                 140

Arg Asp Thr Val Cys Gln Cys Lys Glu Gly Thr Phe Arg Asn Glu Asn
145                 150                 155                 160

Ser Pro Glu Met Cys Arg Lys Cys Ser Arg Cys Pro Ser Gly Glu Val
                165                 170                 175

Gln Val Ser Asn Cys Thr Ser Trp Asp Asp Ile Gln Cys Val Glu Glu
            180                 185                 190

Phe Gly Ala Asn Ala Thr Val Glu Thr Pro Ala Ala Glu Glu Thr Met
    195                 200                 205

Asn Thr Ser Pro Gly Thr Pro Ala Pro Ala Ala Glu Glu Thr Met Asn
    210                 215                 220

Thr Ser Pro Gly Thr Pro Ala Pro Ala Ala Glu Glu Thr Met Thr Thr
225                 230                 235                 240

Ser Pro Gly Thr Pro Ala Pro Ala Ala Glu Glu Thr Met Thr Thr Ser
                245                 250                 255

Pro Gly Thr Pro Ala Pro Ala Ala Glu Glu Thr Met Thr Thr Ser Pro
                260                 265                 270

Gly Thr Pro Ala Ser Ser His Tyr Leu Ser Cys Thr Ile Val Gly Ile
            275                 280                 285

Ile Val Leu Ile Val Leu Leu Ile Val Phe Val
    290                 295

<210> SEQ ID NO 4
<211> LENGTH: 250
<212> TYPE: PRT
<213> ORGANISM: Human
```

-continued

```
<400> SEQUENCE: 4

Met Pro Ala Ser Ser Pro Phe Leu Leu Ala Pro Lys Gly Pro Pro Gly
 1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Arg Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 5
<211> LENGTH: 21
<212> TYPE: DNA
<213> ORGANISM: Human

<400> SEQUENCE: 5
cgccccttgc cctgaccact a                                            21

<210> SEQ ID NO 6
<211> LENGTH: 35
<212> TYPE: DNA
<213> ORGANISM: Human

<400> SEQUENCE: 6
gccatttcag atcttaagca gcttattttt actga                             35

<210> SEQ ID NO 7
<211> LENGTH: 65
<212> TYPE: DNA
<213> ORGANISM: Human

<400> SEQUENCE: 7
gccaccatgg aacaacgccc tagaggatgt gctgccgtgg ccgccgcgct cctcctggtg    60
``` ctgct 65

<210> SEQ ID NO 8
<211> LENGTH: 35
<212> TYPE: DNA
<213> ORGANISM: Human

<400> SEQUENCE: 8
tggacccaag atctctgcct ccatccacag acagc 35

<210> SEQ ID NO 9
<211> LENGTH: 27
<212> TYPE: DNA
<213> ORGANISM: Human

<400> SEQUENCE: 9
gccgccgaga tgcaaggggt gaaggag 27

<210> SEQ ID NO 10
<211> LENGTH: 28
<212> TYPE: DNA
<213> ORGANISM: Human

<400> SEQUENCE: 10
atggtgcaag atctgtaatg agaagagg 28

<210> SEQ ID NO 11
<211> LENGTH: 1717
<212> TYPE: DNA
<213> ORGANISM: Human

<400> SEQUENCE: 11
acctctgtcc ttagagggga ctggaaccta attctcctga gcctgaggga gggtggaggg 60
tctcaagaca acgctgtccc cacgacggag tgccaggagc actaacagta cccttagatt 120
gctttcctcc tccctccttt tttattttca agttcctttt tatttctcct tgcgtaacaa 180
ccttcttccc ttctgcacca ctgcccgtac ccttacccgc gccgccacct ccttgctaca 240
ccactcttga aaccacagct gttggcaggg tcccccagct catgccagcc tcatctcctt 300
tcttgctagc ccccaaaggg cctccaggca acatgggggg cccagtcaga gagccggcac 360
tctcagttgc cctctggttg agttgggggg cagctctggg ggccgtggct tgtgccatgg 420
ctctgctgac ccaacaaaca gagctgcaga gcctcaggag agaggtgagc cggctgcaga 480
ggacaggagg cccctcccag aatgggaagg ggtatccctg gcagagtctc ccggagcaga 540
gttccgatgc cctggaagcc tgggagaatg gggagagatc ccggaaaagg agagcagtgc 600
tcacccaaaa acagaagaag cagcactctg tcctgcacct ggttcccatt aacgccacct 660
ccaaggatga ctccgatgtg acagaggtga tgtggcaacc agctcttagg cgtgggagag 720
gcctacaggc ccaaggatat ggtgtccgaa tccaggatgc tggagtttat ctgctgtata 780
gccaggtcct gtttcaagac gtgacttca ccatgggtca gtggtgtct cgagaaggcc 840 aaggaaggca ggagactcta ttccgatgta taagaagtat gccctcccac ccggaccggg 900
cctacaacag ctgctatagc gcaggtgtct tccatttaca ccaagggat attctgagtg 960 tcataattcc ccgggcaagg gcgaaactta acctctctcc acatggaacc ttcctggggt 1020
ttgtgaaact gtgattgtgt tataaaaagt ggctcccagc ttggaagacc agggtgggta 1080
catactggag acagccaaga gctgagtata taaaggagag ggaatgtgca ggaacagagg 1140

-continued

```
cgtcttcctg ggtttggctc cccgttcctc acttttccct tttcattccc accccctaga    1200
ctttgatttt acggatatct tgcttctgtt ccccatggag ctccgaattc ttgcgtgtgt    1260
gtagatgagg ggcggggggac gggcgccagg cattgtccag acctggtcgg ggcccactgg   1320
aagcatccag aacagcacca ccatctagcg gccgctctag aggatccctc gagggccca    1380 agcttacgcg tgcatgcgac gtcatagctc tctccctata gtgagtcgta ttataagcta   1440
gcttgggatc tttgtgaagg aaccttactt ctgtggtgtg acataattgg acaaactacc   1500
tacagagatt taaagctcta aggtaaatat aaaattttta agtgtataat gtgttaaact   1560
agctgcatat gcttgctgct tgagagtttg gcttactgag tatgattatg aaaatattat   1620
acacaggagc tagtgatcta tgttggtttt agatcaagcc aaggtcattc aggcctcagc   1680
tcaagctgtc atgatcatat cagcatacaa ttgtgag                            1717
```